United States Patent [19]

Tobler et al.

[11] Patent Number: 5,448,069
[45] Date of Patent: Sep. 5, 1995

[54] INFRARED MEASUREMENT OF CONSTITUENTS OF PARTICULATE FOODSTUFFS

[75] Inventors: Hans Tobler, Algetschausen; Peter Perten, Sarnen, both of Switzerland

[73] Assignee: Buhler AG Maschinenfabrik, Switzerland

[21] Appl. No.: 96,681

[22] Filed: Jul. 23, 1993

Related U.S. Application Data

[63] Continuation-in-part of Ser. No. 960,451, Feb. 22, 1993.

[30] Foreign Application Priority Data

Apr. 23, 1991 [SE] Sweden .................................. 9101220

[51] Int. Cl.⁶ ............................................. G01N 21/35
[52] U.S. Cl. ................................ 250/339.01; 250/339.02; 250/339.11; 250/339.12; 250/341.8; 250/910
[58] Field of Search .................. 250/339.01, 339.02, 250/339.06, 339.09, 339.11, 339.12, 341, 343, 359.1, 910, 341.1, 341.5, 341.8

[56] References Cited

U.S. PATENT DOCUMENTS

| | | | |
|---|---|---|---|
| 3,776,642 | 12/1973 | Anson et al. | |
| 3,828,173 | 8/1974 | Knepler | 250/910 X |
| 4,040,747 | 8/1977 | Webster | 250/910 X |
| 4,253,766 | 3/1981 | Funk | 250/910 X |
| 4,260,262 | 4/1981 | Webster | 250/910 X |
| 4,286,237 | 8/1981 | James | |
| 4,400,086 | 8/1983 | Webster | 356/36 |
| 4,404,642 | 9/1983 | Rosenthal | |
| 4,422,760 | 12/1983 | Webster | 356/244 |
| 4,466,076 | 8/1984 | Rosenthal | |
| 4,479,055 | 10/1984 | Perten | 250/343 X |
| 4,540,286 | 9/1985 | Satake et al. | |
| 4,563,581 | 1/1986 | Perten | |
| 4,640,614 | 2/1987 | Roberts et al. | |
| 4,734,584 | 3/1988 | Rosenthal | |
| 4,742,228 | 5/1988 | Bischoff | 250/910 X |
| 4,752,689 | 6/1988 | Satake | |
| 4,866,644 | 9/1989 | Shenk et al. | |
| 4,883,963 | 11/1989 | Kemeny et al. | |
| 4,963,743 | 10/1990 | Satake et al. | |
| 5,155,545 | 10/1992 | Rinke | 356/437 X |
| 5,220,168 | 6/1993 | Adamski et al. | 250/341 X |
| 5,308,981 | 5/1994 | Perten | 250/358.1 |

FOREIGN PATENT DOCUMENTS

| | | |
|---|---|---|
| 0240185 | 10/1987 | European Pat. Off. |
| 0304232 | 2/1989 | European Pat. Off. |
| 0179108 | 7/1989 | European Pat. Off. |
| 179108 | 7/1989 | European Pat. Off. |
| 0388082 | 9/1990 | European Pat. Off. |
| 0404562 | 12/1990 | European Pat. Off. |
| 3024794 | 1/1982 | Germany |
| 8500656 | 2/1985 | WIPO |
| 8504957 | 11/1985 | WIPO |
| WO03/01310 | 1/1994 | WIPO |

OTHER PUBLICATIONS

"Near-Infrared Reflectance Analysis", Analytical Chemistry, vol. 55, No. 12, Oct. 1983, by D. Wetzel, pp. 1165A–1176A.

"Characteristics of Non-Destructive Near-Infrared Instruments For Grain and Food Products", 1985 Meeting Japan Food Science Institute, by Robert D. Rosenthal, pp. 1–23.

Primary Examiner—Constantine Hannaher
Assistant Examiner—Edward J. Glick
Attorney, Agent, or Firm—Finnegan, Henderson, Farabow, Garrett & Dunner

[57] ABSTRACT

A particulate foodstuff in a production line is compacted and caused to travel past a measuring device in a continuous stream. As the stream moves by the measuring device, the latter exposes successive portions of the stream to near infrared light having a spectrum of wavelengths. Each portion is exposed for less than 100 milliseconds. The stream reflects light and at least part of the reflected light is detected by sensors which generate signals. The signals are statistically averaged to yield, in conjunction with calibration values, average concentrations for the constituents of the foodstuff.

22 Claims, 7 Drawing Sheets

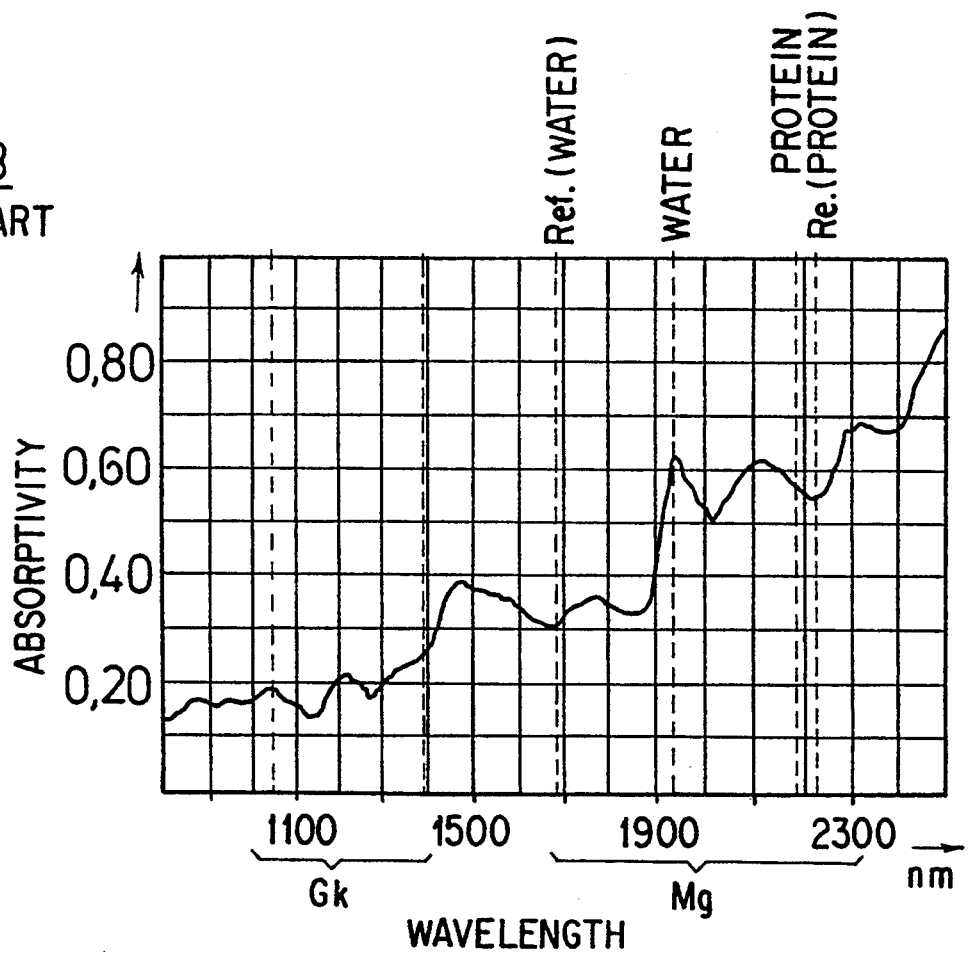
FIG 3 PRIOR ART
FIG 4
FIG 5 PRIOR ART
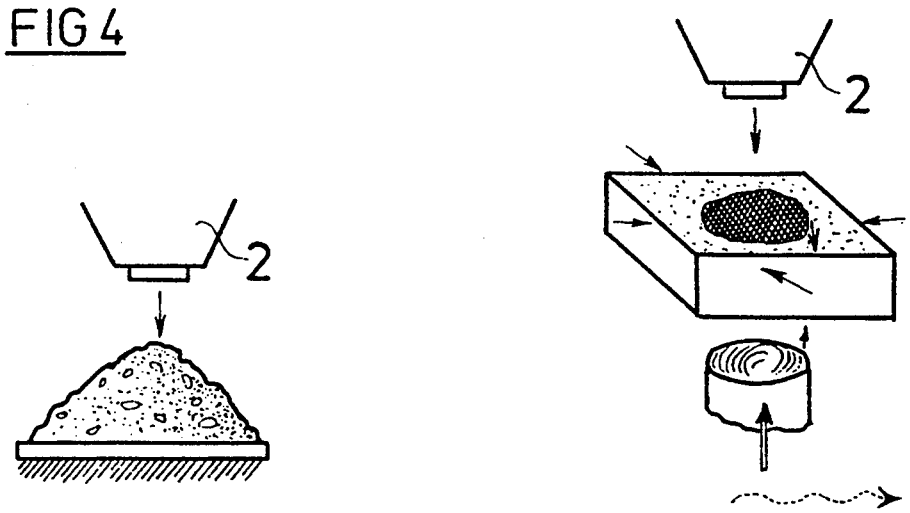

INFRARED MEASUREMENT OF CONSTITUENTS OF PARTICULATE FOODSTUFFS

CROSS REFERENCE TO RELATED APPLICATION

This application is a continuation-in-part of International Application PCT/CH92/00080 filed Apr. 23, 1992, and U.S. patent application Ser. No. 07/960,451 filed Feb. 22, 1993, for "Process and Device for the In-Line NIR Measurement of Pourable Foodstuffs".

BACKGROUND OF THE INVENTION

The invention relates generally to the determination of the constituents of flowable particulate substances.

More particularly, the invention relates to the determination of the constituents of flowable particulate substances, especially of flowable particulate foodstuffs, using infrared radiation.

A variety of methods is employed to measure the concentration of a constituent of a flowable particulate substance. Examples are NMR, microwave and capacitive measuring methods. In practice, however, only a few of these methods are in widespread use, some for the measurement of a single constituent only.

It is known to measure the moisture of whole grain kernels by means of microwaves. Much more common in the grain processing industry, however, is the capacitive measurement of moisture content as described, for instance, in the present assignee's German Offenlegungsschrift 30 24 794. This method makes it possible to determine the moisture content of whole grain kernels, and to moistening to a predetermined moisture content, with a high degree of precision.

Capacitive measurement is carried out with a plate capacitor having a large area. The sample is advantageously conveyed past the capacitor plates which is ideal for an in-line measurement, that is, a measurement in the production line. By appropriate design of the measuring passage, average sample values can be obtained.

For the on-line measurement of the moisture content flour and semolina with NIR (near infrared radiation), the sample must be handled in an opposite manner. Thus, NIR measurement requires not only a light source but also an optical system so that NIR measurement is a form of point measurement. Each movement, whether by the optical system or by the sample, creates problems and can cause fuzziness in the representation of the surface condition of the sample.

These problems are effectively eliminated by subjecting the sample to predetermined conditions, e.g., as regards pressure and density, for the NIR measurement and, in addition, stopping the sample during the measurement as in the laboratory. The present assignee has been able to apply such a measuring procedure in practice with good results (European Patent Application 0 179 108). However, this procedure has the drawback that it is not possible to measure whole kernels, e.g., to determine the protein content of whole grain kernels. This leads to the following undesirable situation:

the moisture content of whole kernels is determined by a capacitive or, if necessary, microwave measuring technique, the protein content of flour is determined by the NIR measuring technique, and the protein content of whole kernels must be determined in the laboratory.

Furthermore, there are currently many special devices for on-line measurement of intermediate mill products, e.g., to determine product color. A calibration is carried out with a calibrating specimen in order to correct for all interfering parameters.

A great drawback of these devices stems from the fact that they require the use of three to five fundamentally different wavelength ranges, from gamma rays to microwaves, in a single production plant such as a mill. Thus, the measurement results can frequently be compared only with great difficulty although the product, which is initially in the form of whole kernels and later in the form of semolina or flour, remains basically the same.

SUMMARY OF THE INVENTION

It is an object of the invention to provide a method which allows various forms of a flowable particulate substance to be measured by the same technique.

Another object of the invention is to provide a method which makes it possible to measure different forms of a flowable particulate substance using a single type of radiation.

An additional object of the invention is to provide a method which enables a flowable particulate substance to be measured in a production line.

A further object of the invention is to provide an apparatus which permits various forms of a flowable particulate substance to be measured by a common technique.

It is also an object of the invention to provide an apparatus which makes it possible to measure different forms of a flowable particulate substance using just one type of radiation.

Yet another object of the invention is to provide an apparatus which allows a flowable particulate substance to be measured in a production line.

The preceding objects, as well as others which will become apparent as the description proceeds, are achieved by the invention.

One aspect of the invention resides in a method of determining the concentration of a constituent of a flowable particulate substance, particularly of a flowable particulate foodstuff. The method comprises the steps of advancing a stream of the particulate substance along a predetermined path, irradiating each of different portions of the stream over an infrared spectral range at a predetermined location of the path, and measuring, at selected wavelengths in the spectral range, infrared radiation deflected by each portion. The irradiating steps are carried out during the advancing step. The method further comprises the step of calculating the concentration of the constituent, and the calculating step involves an averaging of measurements obtained during the measuring steps.

The irradiating steps can be performed in-line. The method can then be used for the continuous in-line measurement of the particulate substance. The spectral range employed for the irradiating steps is advantageously the near infrared range. Each portion of the stream is preferably irradiated for less than 100 milliseconds and, more favorably, for less than 50 milliseconds.

The particulate substance is advantageously compacted or compressed prior to the irradiating steps.

The irradiating steps for different portions of the stream can be performed successively and the same holds true for the measuring steps. The measuring steps may include measurement of infrared radiation reflected by the various portions of the stream.

The averaging of the measurements obtained during the measuring steps may be a statistical averaging. In addition to the averaging, calculation of the concentration of the constituent may involve the use of a calibration value.

The speed of the stream may be adjustable and the advancing step may comprise conveying each portion of the stream through the predetermined measuring location at substantially the same preselected speed. For granular substances which flow easily, the speed of the stream through the predetermined location is preferably regulated using a screw conveyor. On the other hand, a dosing vibratory element is advantageously used to regulate the speed of the stream through the predetermined location when the particulate substance is floury and does not flow readily.

The stream may contain particles of predetermined length and, in accordance with one embodiment of the method, each portion of the stream is irradiated for a time interval shorter than that during which such portion advances one-tenth of the predetermined length. To achieve this, the irradiating time and speed of the stream are appropriately adjusted relative to one another. This embodiment of the method is particularly well-suited for specific types of substances.

The measuring step for each portion of the stream may involve simultaneous measurement of radiation of the different wavelengths. Advantageously, the measuring steps are here performed using the diode array principle. This allows the measurement accuracy to be increased and makes it possible for the main elements of the measuring means to remain stationary during the measurements. Essentially no moving parts are required.

Alternatively, the measuring step for each portion of the stream may involve measuring radiation of the different wavelengths in rapid succession. The calculating step may then include a statistical evaluation of correlated measurements obtained from the measuring steps.

The method may further comprise the step of baffling or damming the stream in a section of the predetermined path upstream of the measuring location. The stream is preferably substantially continuous or unbroken in this section of the path.

The baffling step, which can be performed so as to be essentially pressureless, may comprise automatic regulation of the flow rate of the substance. The baffling step may result in an accumulation of the particulate substance which can be used to determine the throughput of the substance. The accumulation may be formed in a main feed pipe or a bypass pipe, advantageously by means of a dosing screw conveyor of adjustable speed.

The irradiating steps may involve directing infrared radiation towards the accumulated substance of the stream along a first direction and the advancing step then preferably comprises conveying the stream through the measuring location along a second direction transverse or normal to the first direction.

Another aspect of the invention resides in an apparatus for determining the concentration of a constituent of a flowable particulate substance, particularly of a flowable particulate foodstuff. The apparatus, which can be designed to continuously determine the concentration of the constituent, comprises means for uninterruptedly directing a stream of the substance along a predetermined path; means for irradiating the stream with infrared radiation at a predetermined location of the path; means for measuring infrared radiation deflected by the stream; and means for calculating the concentration of the constituent based on data from the measuring means.

The directing means may comprise a tubular element which defines a continuous, tubular measuring section or channel for the stream. The directing means can also include means for forcibly advancing or moving the stream along the predetermined path relative to the irradiating means and such advancing means is preferably adjustable.

The irradiating means, which advantageously emits radiation in the near infrared wavelength range, can be regulated so as to repeatedly irradiate the stream, i.e., so as to irradiate the stream a large number of times, for respective periods of less than about 1.00 milliseconds, preferably less than about 50 milliseconds. The calculating means is here designed to statistically determine an average concentration of the constituent.

The measuring means may comprise a diode array for the simultaneous measurement of radiation of different wavelengths. Alternatively, the measuring means may include a rotatable carrier, and a plurality of filters on the carrier for transmitting radiation of different wavelengths. In this manner, successive measurement of radiation of different wavelengths can be achieved.

The apparatus can further comprise means for rotating the carrier at a speed in excess of 10 revolutions per second, preferably in excess of 25 revolutions per second.

It has already been possible to achieve measurements of high accuracy with an experimental apparatus according to the invention. This is surprising since the invention departs completely from the traditional laboratory procedure of preparing a sample, holding the sample stationary, recording several values from the sample and averaging the values. All that is necessary for the invention is a dense, homogeneous stream and an accompanying reproducible surface condition of the sampled portions of the stream. The sampled portions must be moved relative to the measuring means, preferably forwards in the direction of product flow. A large number of individual measurements is made but now on constantly changing samples. Thus, varying results are knowingly obtained.

It is of advantage to make a large number of individual measurements so that the concentration or concentrations of one or more constituents, depending upon the selected wavelength range or ranges, can be calculated using statistical averaging. The time for an individual measurement can be less than 100 milliseconds and is preferably less than 50 milliseconds.

In accordance with the invention, averaging is done twice. Thus, an average is taken over time and also over different samples. In spite of the movement of the product and the very short irradiation times, measurements of better quality than heretofore can be achieved.

Particularly surprising is the fact that even with whole kernels the concentrations of the constituents can be obtained with great accuracy. For the first time, it has become possible to determine in-line the concentrations of different constituents such as water, protein and ash, and also product color, with the same system. This applies to floury as well as granular products. In a mill, a single measuring principle for constituent concentration can therefore be employed from the storage area for the whole kernels through the intermediate processing stages and to the final production stage. Accordingly, directly comparable measurements can be obtained without difficulty. This greatly facilitates mill administration and allows greater automation to be achieved than in the prior art.

For the practical worker in the art, the invention provides a testing method which is well-suited for products having substantial inhomogeneity and is especially useful for control functions, e.g., for influencing the contents of individual constituents. Thus, similarly to a quantity of material which is held in the hands and can be viewed and evaluated from many sides, the product in the method of the invention is moved during viewing and a sufficient number of samples are observed. A particular advantage of the method of the invention resides in that measurements can be obtained from overlapping samples. In any event, however, a relatively large number of measurements should be made. Based on empirical results, it is preferred for the number of individual measurements to exceed 30.

That which creates difficulty in the known NIR measuring techniques is now turned to advantage in that the product moves past the measuring means during measurement.

In a mill, the product is constantly in motion for processing and, according to the invention, this serves as the basis for a determination of the constituents of the product. Thus, a large number of measurements are obtained over time as well as from different samples. The number of measurements is at least 10 to 15 and, as mentioned previously, preferably exceeds 30. From these measurements, the desired average concentrations of the constituents are calculated using statistical calculating methods. In the event of a deviation from a reference value, the invention makes it possible to take immediate remedial action in the production line or at individual processing stations since errors are determined within seconds.

The novel features which are considered as characteristic of the invention are set forth in particular in the appended claims. The improved infrared measuring method, as well as the construction and mode of operation of the improved infrared measuring apparatus, together with additional features and advantages thereof, will, however, be best understood upon perusal of the following detailed description of certain specific embodiments when read in conjunction with the accompanying drawings.

BRIEF DESCRIPTION OF THE DRAWINGS

FIG. 3 illustrates a conventional NIR absorption spectrum;

FIG. 4 schematically shows a randomly formed pile of a flowable particulate substance;

FIG. 5 schematically illustrates the compression of a flowable particulate substance in accordance with the prior art;

DESCRIPTION OF THE PREFERRED EMBODIMENTS

Figure 1:
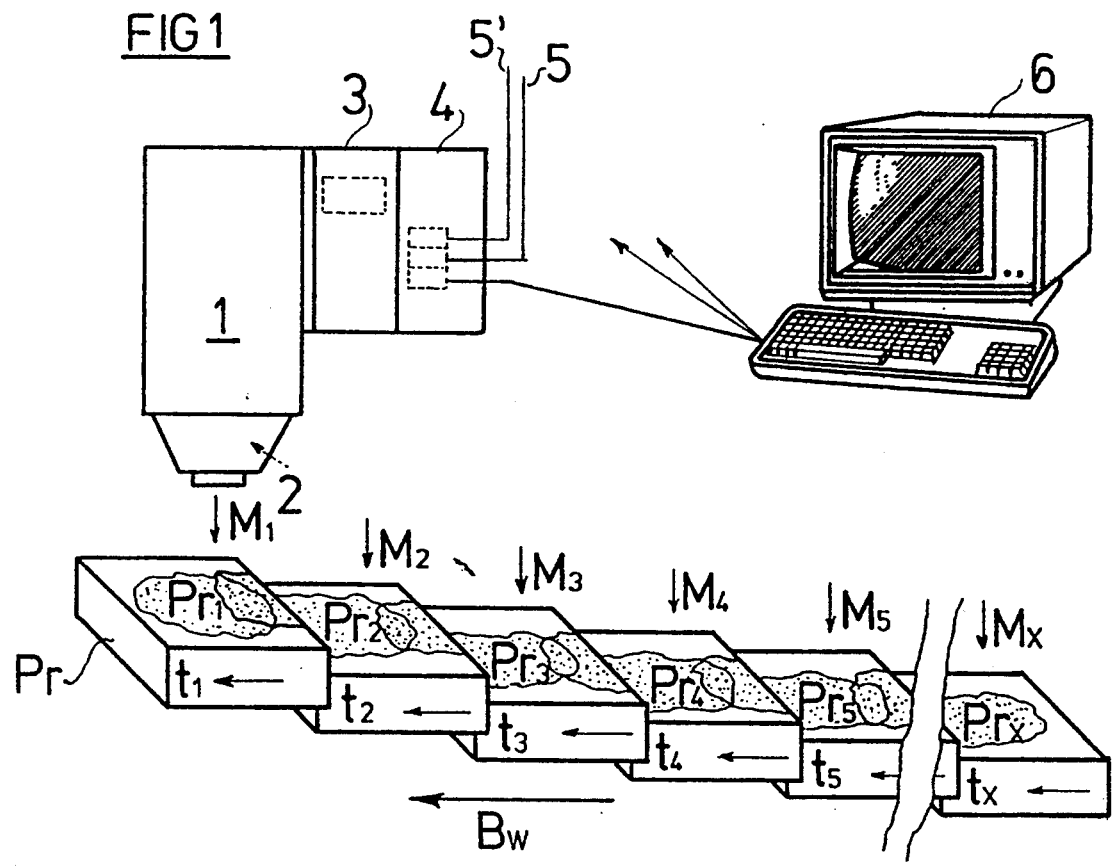
FIG. 1 schematically illustrates one embodiment of an infrared measuring apparatus in accordance with the invention.

FIG. 1 illustrates an apparatus according to the invention for the continuous in-line measurement of the constituent content of a flowable particulate substance or product Pr using near infrared radiation (NIR). The product Pr, which can range in character from granular to floury, is here assumed to be a foodstuff.

The term "in-line" is to be distinguished from "on-line". In this regard, the term "on-line" is understood to mean the making of measurements in the vicinity of the production line. "On-line" leaves open the possibility that a sample of a product is removed completely from the production line and measured externally thereof.

On the other hand, "in-line" means that a product is measured in a processing machine, a main feed pipe or an active bypass pipe. With an in-line measurement, there is no removal of a sample from the production line although some of the product may be detoured from the actual production line and subsequently returned thereto.

The general problems associated with on-line and in-line measurements are known. Removal of a sample from the production line in on-line measurement raises the question of the representativeness of the sample. For in-line measurement, it is important to properly select the location at which measurements are made.

Referring to FIG. 1, the reference numeral 1 identifies a measuring device containing an optical system and having a measuring head 2. An electronic control unit 3 is connected to the measuring device 1 and also to a transducer 4. The transducer 4, in turn, is connected to a computer 6, e.g., a PC. Two conductors 5 and 5' for the transmission of signals extend from the transducer 4.

The product Pr defines a stream which moves uninterruptedly or continuously from right to left along a predetermined path Bw in a production line. The path Bw passes directly beneath the measuring head 2 which is stationary. The product stream Pr is compacted upstream of the measuring head 2.

At time t1, a segment or portion Pr1 of the product stream Pr is located below the measuring head 2, and a measurement M1 is made on the stream segment Pr1 using near infrared radiation. The product stream Pr continues to move during the measurement M1. The measurement M1 is preferably carried out as rapidly as possible, i.e., the measurement M1 is preferably performed in a manner resembling the taking of a flash photograph.

Additional measurements M2,M3,M4,M5...Mx are respectively made on additional segments or portions Pr2,Pr3,Pr4,Pr5...Prx of the product stream Pr at the respective times t1,t2,t3,t4,t5...tx that the segments Pr1,Pr2,Pr3,Pr4,Pr5...Prx are located below the measuring head 2. Similarly to the measurement M1, it is preferred that the measurements M2,M3,M4,M5...Mx be carried out as rapidly as possible.

The time for performing an individual measurement M1 or M2 or M3...can be less than 100 milliseconds and is advantageously less than 50 milliseconds. If the product stream Pr is granular and contains particles of predetermined length, the flow rate of the product stream Pr and the time for performing an individual measurement M1 or M2 or M3...can be adjusted relative to one another such that the stream segment Pr1 or Pr2 or Pr3...advances less than one-tenth of the predetermined length during the respective measurement M1 or M2 or M3...

The individual measurements M1 or M2 or M3... are transmitted to the computer 6 via the optical system of the measuring device 1 and via the control unit 3, e.g., over a period of 10 seconds. The computer 6 statistically averages the series of measurements M1,M2,M3,M4,M5...Mx to thereby obtain average concentrations for the constituents of the product stream Pr. The number of measurements M1,M2,M3,M4,M5...Mx which are averaged depends upon the objective and can range from several dozen to the hundreds.

Figure 2:
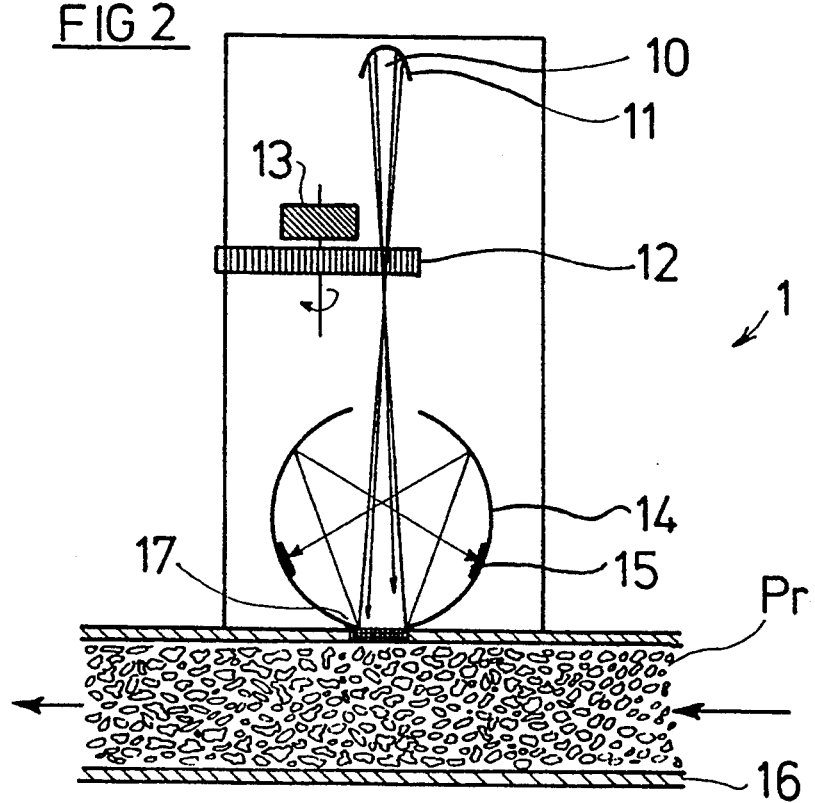
FIG. 2 is an enlarged view of an infrared measuring device constituting part of the apparatus of FIG. 1.

FIG. 2 is an enlarged view of the measuring device 1 and illustrates certain details of the optical system for performing NIR measurements. The measuring device 1 includes a housing which accommodates a light source 10 and an ellipsoidal mirror or reflector 11 for directing light from the source 10 towards the product stream Pr. The housing of the measuring device 1 further accommodates a filter wheel 12, a motor 13 for rotating the filter wheel 12, an Ulbricht sphere 14 and light sensors 15.

A large number of filters, e.g., 6, 12 or 24, is disposed circumferentially of the filter wheel 12. Each filter transmits near infrared radiation of a different wavelength and the filters are selected so as to embrace a desired spectrum or wavelength range. During a measurement M1,M2,M3,M4,M5...Mx, the respective stream segment Pr1,Pr2,Pr3,Pr4,Pr5...prx is exposed to radiation of each wavelength.

The motor 13 is designed to drive the filter wheel 12 at relatively high speed. The filter wheel 12 is rotated at a speed in excess of 10 revolutions per second, preferably at a speed in excess of 25 revolutions per second.

FIG. 2 shows the product stream Pr advancing through a feed pipe 16. The feed pipe 16 is provided with a window 17 at the measuring device 1 in order to permit irradiation of the product stream Pr for measurement. The product stream Pr is compared with a reference as in calibration.

FIG. 3 illustrates a conventional absorption spectrum for a floury product. A pair of values, including a reference value, is indicated for both water and protein. In the illustrated example, the values for water lie at a wavelength above 1900 nm while those for protein are above 2200 nm.

Depending upon the construction of the measuring device, e.g., the selection of appropriate filters, the values for water and protein, that is, the water content and protein content, can be determined simultaneously or successively.

FIG. 4 shows a randomly poured heap of a flowable particulate product. Experiments with the invention have confirmed the finding that measurements from such a randomly poured heap are not representative of the product. Thus, as brought out by FIG. 4, each pouring change generates a measuring error.

FIG. 5 illustrates the method for controlled compression of a sample as taught in the European Patent Application 0 179 108. This method can be successfully employed with floury products only.

Figure 6:
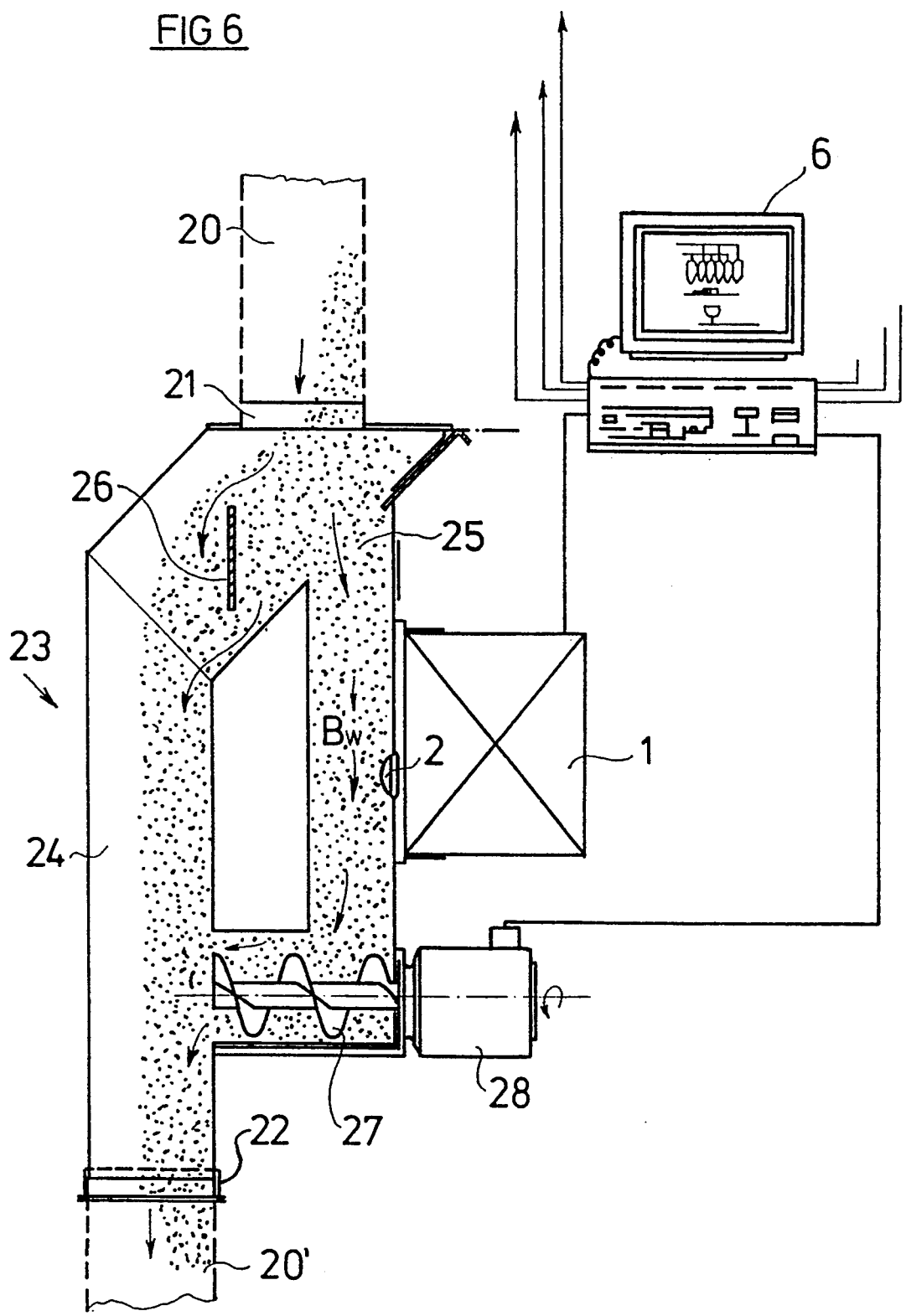
FIG. 6 schematically shows another embodiment of an infrared measuring apparatus according to the invention.

FIG. 6 shows another embodiment of an apparatus according to the invention for the continuous in-line measurement of the constituent content of a flowable particulate substance or product using NIR. In FIG. 6, the reference numeral 20 identifies a feed pipe constituting part of a production line. A tubular measuring insert 23 is provided in the feed pipe 20. The insert 23 has an inlet end which is joined to the feed pipe 20 by a connection 21 and an outlet end which is joined to the feed pipe 20 by a connection 22. The insert 23 splits into a main channel 24 and a measuring or bypass channel 25 a short distance downstream of the inlet connection 21, and the measuring device 1 is mounted adjacent to the measuring channel 25. The main channel 24 and measuring channel 25 rejoin just upstream of the outlet connection 22.

The main channel 24 has essentially the same cross-sectional area as the feed pipe 20 so that, at maximum throughput, all of the product can flow through the main channel 24. A baffle plate 26 is disposed in the region of the split between the main channel 24 and the measuring channel 25 and serves to force part of the product into the measuring channel 25. In this manner, a compacted product stream is formed in the measuring channel 25.

The compacted product stream in the measuring channel 25 is caused to move past the measuring head 2 of the measuring device 1 with the assistance of a regulated discharge screw conveyor 27. The screw conveyor 27 is driven by a motor 28 which is preferably adjustable in a stepless fashion and is controlled by the computer 6. The screw conveyor 27 makes it possible for the product stream to advance through the measuring channel 25 at a controllable, preselected speed so that movement of the product stream can be adjusted to the particular conditions. When a specific rotational speed is selected for the screw conveyor 27, the latter allows the product stream to descend in the measuring channel 25 at a constant rate.

With respect to the measuring insert 23, it is interesting that, contrary to the original assumptions, very good results are achieved for the forcible return of friable particulate products such as whole grain kernels to the main channel 24. This is so in spite of the fact that the measuring insert 23 was initially conceived for floury products. For granular products, it is preferred to employ the measuring insert 23 and its screw conveyor 27.

Figure 7:
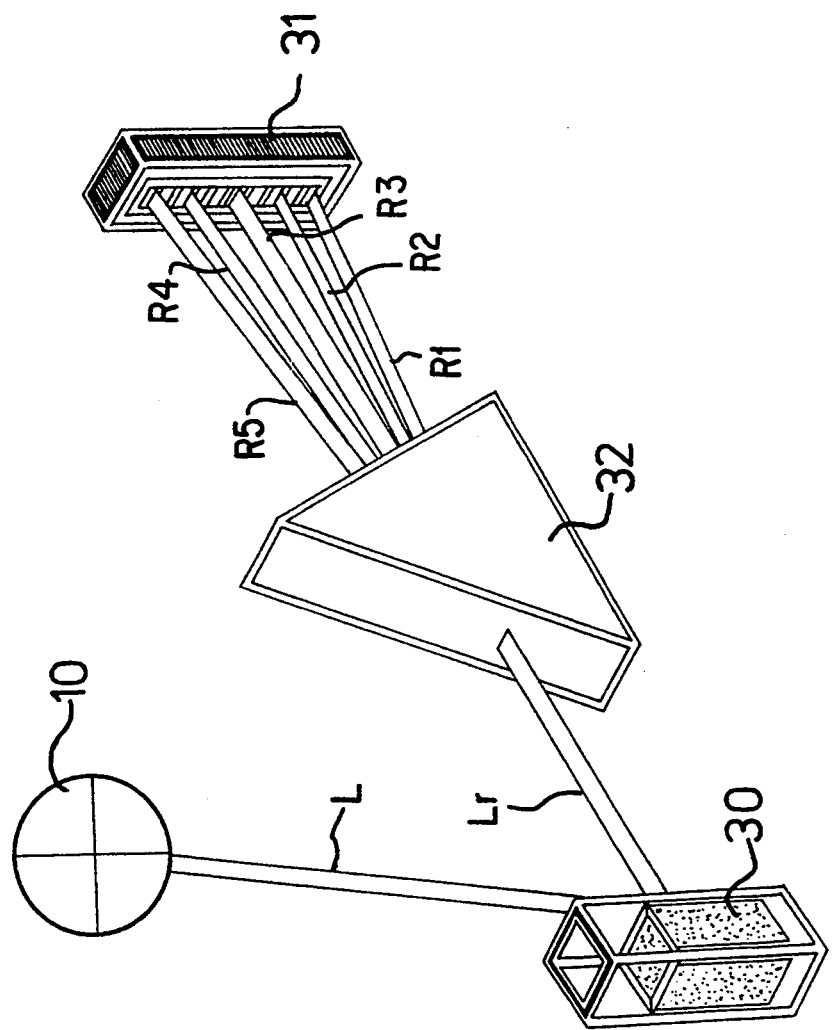
FIG. 7 schematically illustrates a second infrared measuring device.

FIG. 7 illustrates the use of the diode array principle for analysis of a product. A product stream advances through a flow passage 30 and is irradiated by a light beam L from the light source 10. When the beam L impinges the product stream, the latter produces a reflected light beam Lr which is to be analyzed in order to evaluate the constituents of the product stream.

The reflected beam Lr travels to a polychromator or dispersion element 32 which spectrally dissociates the reflected beam Lr locally, that is, splits up the reflected beam Lr into component rays R1,R2,R3,R4,R5 having different wavelengths. The rays R1,R2,R3,R4,R5 are transmitted to a detector 31 containing an array of photosensitive diodes and each of the rays R1,R2,R3,R4,R5 impinges a respective diode. The wavelength resolution obtainable with the detector 31 can be adjusted by varying the number of diodes.

The polychromator 32 which, for instance, may be in the form of a holographic grid, can be encased together with the detector 31.

The diode array principle makes it possible to measure all desired wavelengths simultaneously. A great advantage of the diode array principle is that no moving parts are required with the possible exception of a reflector to deflect in a reference beam.

Figure 8:
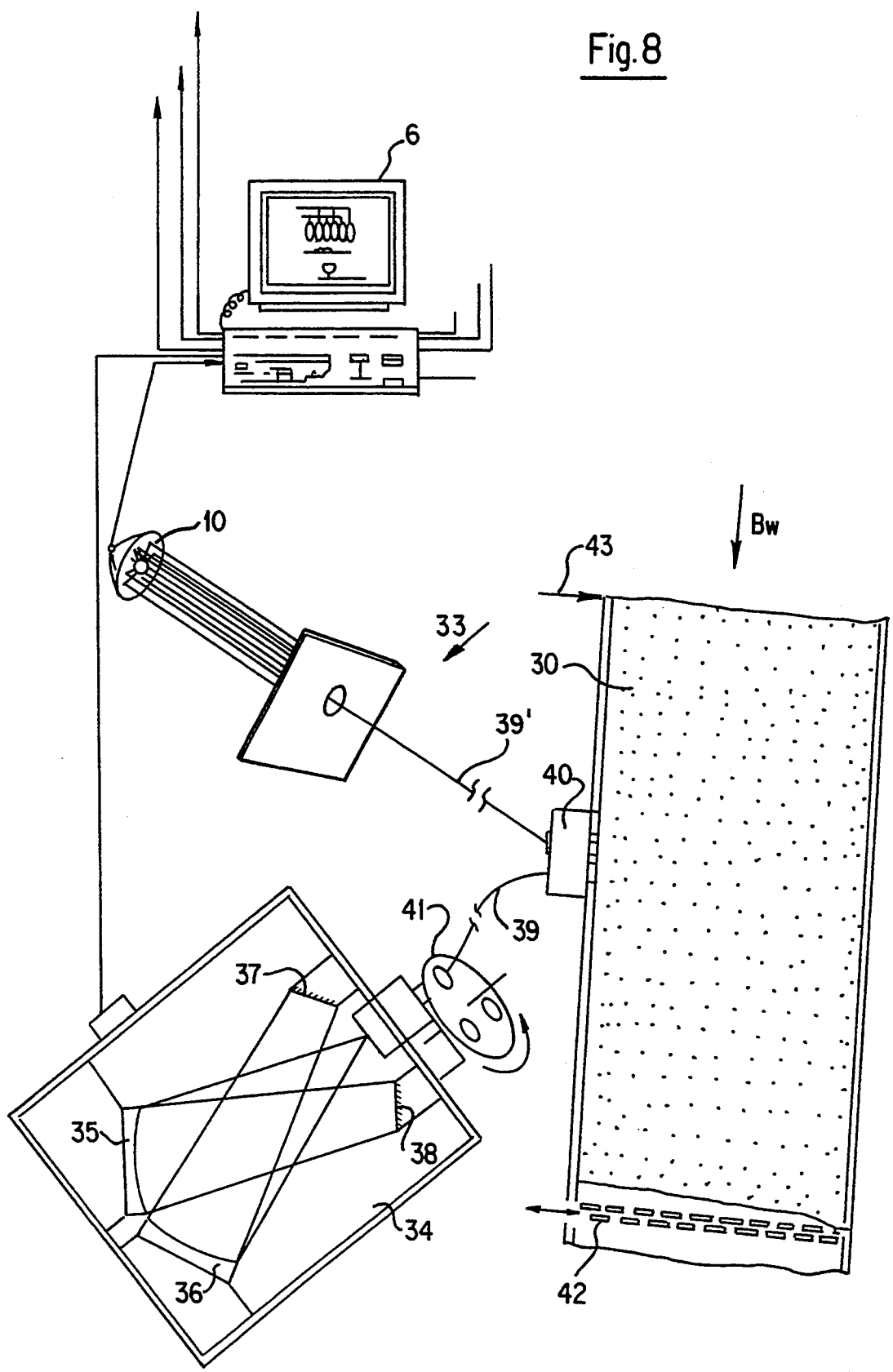
FIG. 8 schematically shows an additional embodiment of an infrared measuring apparatus in accordance with the invention.

FIG. 8 shows an additional embodiment of an apparatus according to the invention for the continuous in-line measurement of the constituent content of a flowable particulate substance or product using NIR. The apparatus of FIG. 8 further employs the diode array principle.

The apparatus of FIG. 8 has a measuring head 40 which is mounted adjacent to a suitable location of the flow passage 30 for the product stream. The apparatus further includes a module 33 which accommodates the light source 10 and a separate sensing module 34. The sensing module 34 contains two holographic grids 35 and 36 as well as two diode arrays 37 and 38.

The light source 10 can be provided with a tungsten halogen lamp, for example. An optical fiber 39' extends from the measuring head 40 towards the light source 10 and serves to conduct light from the source 10 to the head 40 and the product stream.

A second optical fiber 39 extends from the measuring head 40 towards the sensing module 34. The optical fiber 39, which is here shown bent and discontinuous, is preferably composed of fiberglass. In order to obtain distinct individual signals, an interrupter in the form of a perforated disc 41 is advantageously disposed in the region of the optical fiber 39. The perforated disc 41 functions to interrupt the light which travels through the optical fiber 39 to the sensing module 34.

A retaining or dosing device in the form of a vibratory grating 42 is arranged in the flow passage 30 and serves to control the movement of the product stream. A level detector 43 indicated by an arrow is further provided for the flow passage 30.

The apparatus of FIG. 8 exhibits the advantage that the two modules 33 and 34 can be mounted independently at a spacing from the flow passage 30.

Figure 9:
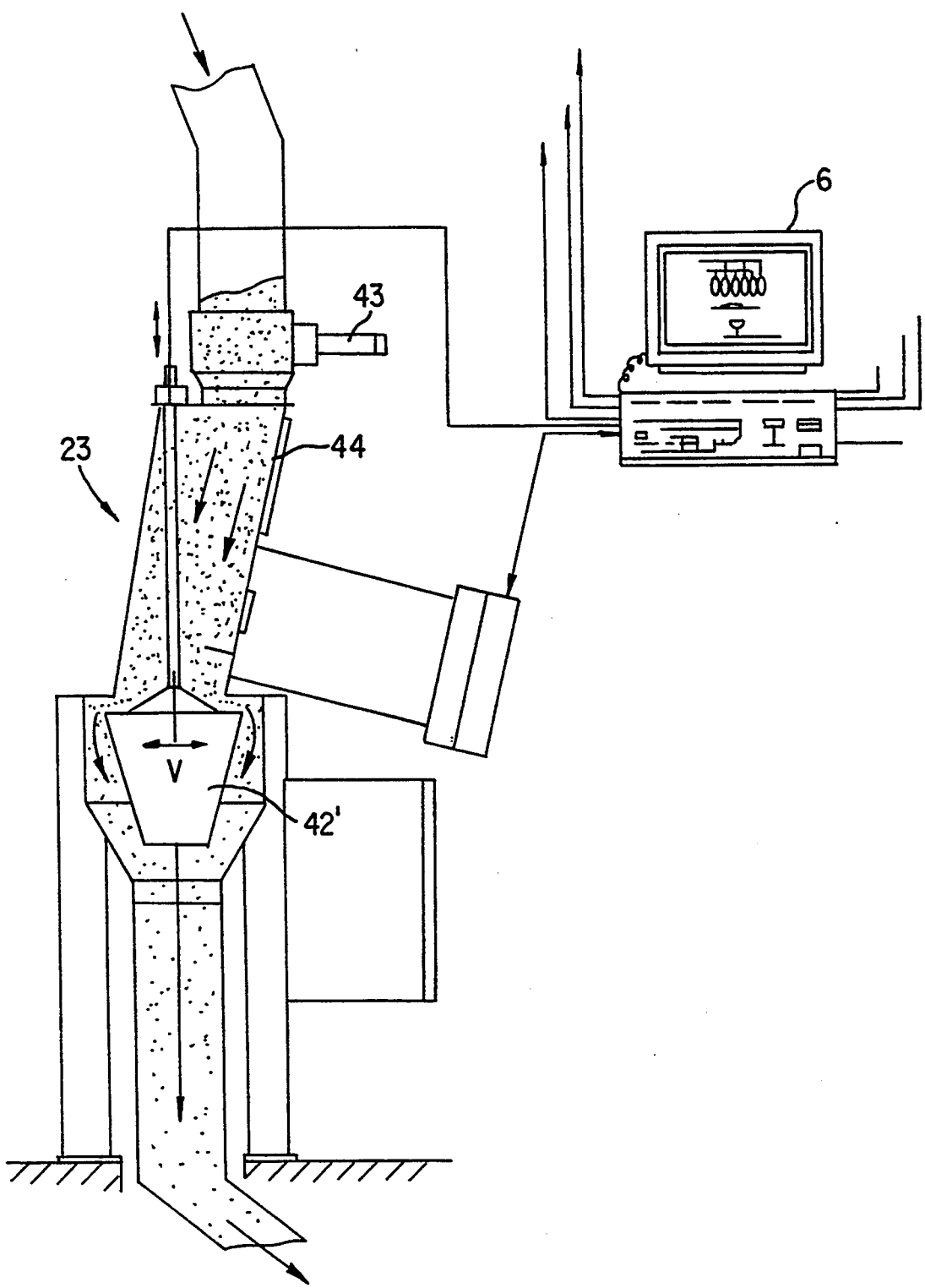
FIG. 9 schematically illustrates a further embodiment of an infrared measuring apparatus according to the invention.

FIG. 9 shows a further embodiment of an apparatus according to the invention for the continuous in-line measurement of the constituent content of a flowable particulate substance or product using NIR. While the apparatus of FIG. 6 with the screw conveyor 27 is preferred for granular products as mentioned earlier, the apparatus of FIG. 9 is preferably used for floury products. The same measuring technique or optical system can be employed in both apparatus and these apparatus differ only in the manner of regulating the movement of the product stream. Thus, each apparatus is best suited to particular flow characteristics.

Depending upon the specific requirements, the measuring insert 23 in the apparatus of FIG. 9 can include a main channel and/or a bypass channel. A conical dosing vibrator 42' mounted inside the measuring insert 23 regulates the discharge of the product from the insert 23. The dosing vibrator 42', which is controlled by the computer 6, is preferably suspended in the measuring insert 23 so as to be adjustable to different heights. This makes it possible to maintain control of the particulate product under all operating conditions. The product stream advantageously has a flow rate of 0.5 cm/sec to 2 cm/sec during measurement.

Movement of the product stream can be monitored via an observation window 44 and adjusted by means of the dosing vibrator 42'.

Figure 10:
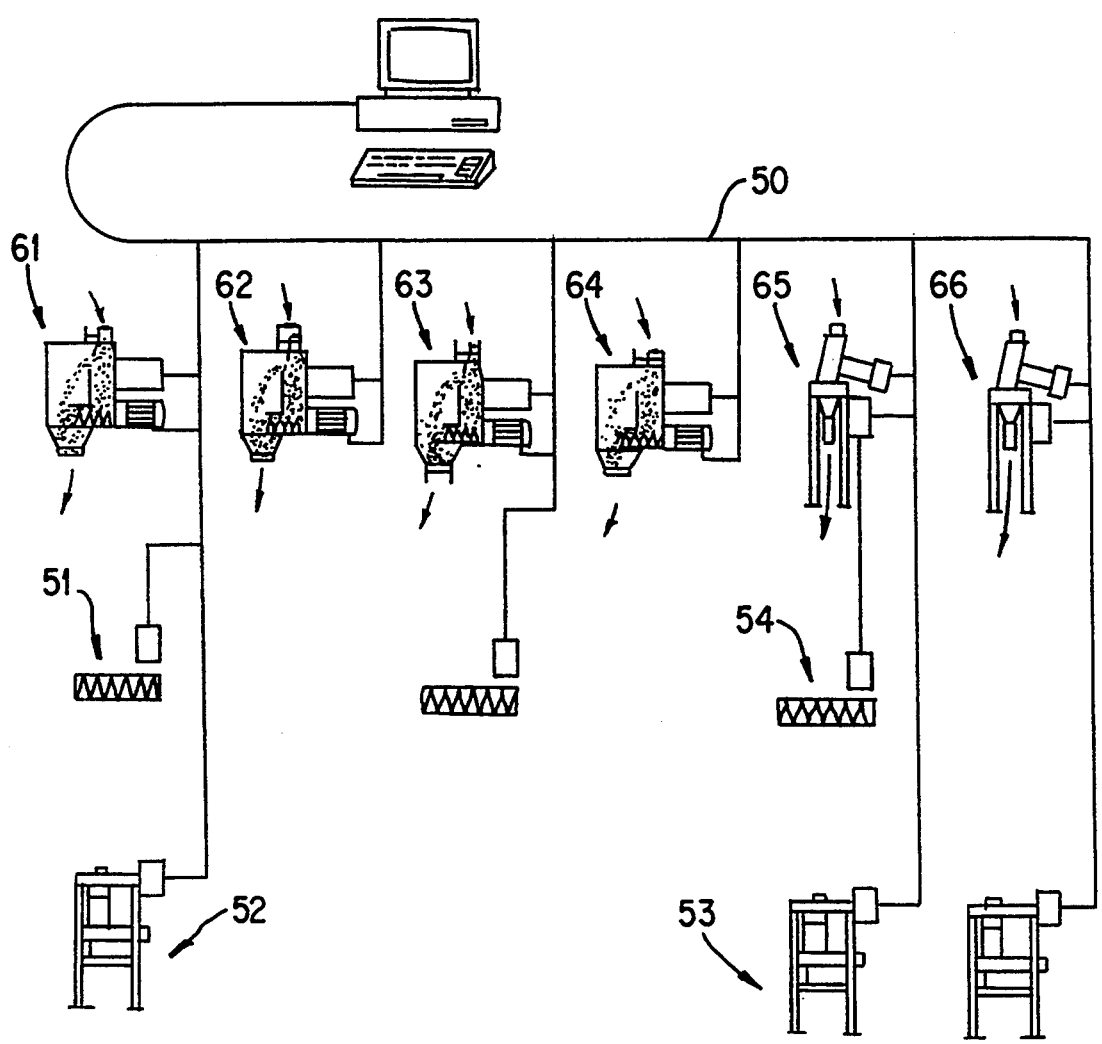
FIG. 10 schematically shows a mill containing infrared measuring apparatus in accordance with the invention.

FIG. 10 illustrates a mill having a group of measuring apparatus in accordance with the invention. In the exemplary showing of FIG. 10, two types of measuring apparatus are present, namely, the measuring apparatus of FIG. 6 and the measuring apparatus of FIG. 9. The measuring apparatus of FIG. 10, which are generally identified by the reference numerals 61,62,63,64,65 and 66, respectively, are adapted to the nature of the product at the particular station of the mill. Among the stations of the mill are a storage station, a cleaning station, a preparatory station for grinding and a station for monitoring the finished product such as flour or semolina.

All of the measuring apparatus 61,62,63,64,65,66 are connected to a central processing unit 6' by means of a bus 50 so that the respective signals can be processed centrally. Appropriate commands can then be sent to the respective control elements.

The measuring apparatus 62 is designed for granular products and can be used, by way of example, to determine the qualitative parameters of incoming product. On the other hand, the measuring apparatus 61, which is likewise designed for granular products, can be used to ascertain moisture content prior to moistening, for instance. The required quantity of water can then be added to the granular product by a moistening device 51. A scale 52 is provided to measure the throughput of the moistened product.

The measuring apparatus 65 is intended for floury products can be used, for example, to measure protein content. Gluten can subsequently be admixed with the floury product via a mixer 54 to achieve a desired concentration. A scale 53 is provided to measure the throughput of the gluten-enriched floury product.

All embodiments of the NIR measuring apparatus according to the invention can have their own computer. Alternatively, several of the NIR measuring apparatus can be connected to a common computer.

Depending upon the particular application, it can be of advantage to calculate average constituent concentrations over a measuring interval of a second, 10 seconds or a minute. Average concentrations calculated over an interval of a second have great advantages for regulating functions whereas average concentrations calculated over longer intervals are advantageous for control purposes.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. A milling process for measuring at NIR wavelengths at different locations in a mill the amount of a constituent of a flowable, particulate foodstuff during in-line processing of the foodstuff, comprising:
   measuring at a first location, using a NIR detection process, during in-line processing of the foodstuff, the amount of a constituent in a first form of said flowable particulate foodstuff;

measuring at a second location separate from said first location, using the same type NIR detection process used at said first location, during in-line processing of the foodstuff, the amount of a constituent in a second form of said flowable particulate foodstuff, said second form of said flowable particulate foodstuff being different from said first form; and calculating the value of the measured constituent for each form of the flowable particulate foodstuff.

2. A milling process as claimed in claim 1, wherein said first form of said flowable particulate foodstuff is unground grain, and the second form is flour.

3. A milling process as claimed in claim 2, wherein the constituent being measured in the unground grain is water and the constituent being measured in the flour is protein.

4. A milling process as claimed in claim 2, wherein said measuring step at each of said first and second locations includes measuring more than one constituent in each of said unground grain and said flour, respectively.

5. A milling process as claimed in claim 1, wherein each measuring step using a NIR detection process includes the steps of:

advancing said particulate foodstuff in a continuous stream along a predetermined path during said in-line processing of said foodstuff;

projecting light at NIR wavelengths onto different portions of said particulate foodstuff as they flow past a predetermined location in said path, said light being reflected from said portions;

detecting the reflected light from said portions of particulate foodstuff at a plurality of NIR wavelengths over a preselected range of NIR wavelengths, and measuring the level of the reflected light at said plurality of wavelengths within said range, the detection of the reflected light over this range of NIR wavelengths occurring in a period of time not greater than 100 ms;

repeating the steps of projecting light at said NIR wavelengths onto different portions of said particulate foodstuff and detecting the light reflected therefrom until detection over the preselected range of NIR wavelengths has occurred a minimum of thirty times, for obtaining a minimum of thirty repeat measurements of the level of reflected light at said plurality of wavelengths within said range.

6. A milling process as claimed in claim 5, wherein each said measuring step further includes obtaining the mean value of the measurements obtained.

7. A milling process as claimed in claim 5, wherein the detection of the reflected light over the range of NIR wavelengths occurs in a period of time not greater than 50 ms.

8. A milling process as claimed in claim 7, wherein the step of advancing a foodstuff includes directing the foodstuff through a pipe in a continuous, in-line, compact, homogeneous stream substantially normal to the light projected onto said foodstuff.

9. A milling process as claimed in claim 5, wherein the step of advancing said foodstuff in a continuous stream includes moving the foodstuff in a compact, homogeneous stream.

10. A milling process as claimed in claim 5, wherein said predetermined path includes a window adjacent to the stream of foodstuff, and the step of projecting light at NIR wavelengths includes projecting said light onto different portions of said foodstuff as it flows past said window; and wherein the step of advancing said foodstuff in a continuous stream includes moving the foodstuff at a controlled rate so that each of the portions flows past said window at substantially the same speed.

11. A milling process as claimed in claim 10, wherein said first form of said flowable particulate foodstuff comprises unground grain kernels, and a single kernel moves less than 1/10 of its length as the reflected light from a portion is being detected.

12. A milling process as claimed in claim 5, wherein the projecting of light at NIR wavelengths onto different ones of said portions includes projecting light at a plurality of specific NIR wavelengths sequentially, and the detection of the reflected light occurs sequentially for the plurality of specific NIR wavelengths within the preselected range.

13. A milling process as claimed in claim 5 further comprising the step of determining the throughput of the foodstuff during in-line processing of the foodstuff.

14. A milling process as claimed in claim 5, wherein said first form of said flowable particulate foodstuff is unground grain and the second form is flour, and said measuring step at each of said first and second locations respectively includes measuring more than one constituent in each of said unground grain and said flour.

15. A milling process as claimed in claim 14 further comprising the step of directing the measurements obtained to a central processing unit and performing in said central processing unit the steps of obtaining the mean values of the measurements obtained and calculating the values of the measured constituents.

16. A milling process as claimed in claim 15 including the additional step of controlling the milling process based on the value obtained for a measured constituent.

17. A milling process as claimed in claim 15, further comprising the step of averaging the calculated values of the measured constituents obtained over a period of at least ten seconds.

18. A mill for processing an unground grain product into a flour product comprising:

a plurality of measuring apparatus connected in said mill at selected locations for the in-line measurement of the constituents of the product in the form in which the product is constituted at each selected location, each selected location having an in-line measurement area;

a central processing unit connected to receive the measurements from said plurality of measuring apparatus and calculate the value of the measured constituents;

each of said measuring apparatus including:

a NIR measuring device positioned adjacent to the in-line measurement area at its respective location for the in-line measurement of the constituents of said product as said product moves past the measurement area; and said NIR measuring device having means for projecting light onto said product as it moves past said measurement area and for detecting the reflected light at a plurality of NIR wavelengths over a preselected range of NIR wavelengths to provide in-line measurements of the level of the reflected light at said plurality of NIR wavelengths.

19. A method of determining the concentration of a constituent of a flowable particulate substance, comprising the steps of:

advancing a stream of said substance along a predetermined path;

irradiating each of different portions of said stream over an infrared spectral range at a predetermined location of said path;

measuring, at selected wavelengths in said range, infrared radiation deflected by each of said portions, the irradiating steps being carried out during the advancing step;

calculating the concentration of said constituent, the calculating step including averaging measurements obtained during the measuring steps; and baffling said stream in a section of said path upstream of said predetermined location.

20. The method of claim 19, wherein said stream is substantially continuous in said section of said path.

21. The method of claim 19, wherein the baffling step is substantially pressureless.

22. The method of claim 19, wherein the irradiating step comprises directing infrared radiation towards said stream along a first direction and the advancing step comprises conveying said stream along a second direction transverse to said first direction.

* * * * *